United States Patent [19]

Effland et al.

[11] Patent Number: 4,931,457
[45] Date of Patent: Jun. 5, 1990

[54] NAPHTHYLAMINO-AND NAPHTHYLOXY-PYRIDINAMINE COMOUNDS USEFUL AS TOPICAL ANTIINFLAMMATORY AGENTS FOR THE TREATMENT OF SKIN DISORDERS

[75] Inventors: Richard C. Effland; Joseph T. Klein, both of Bridgewater; Gordon E. Olsen, Somerset; Larry Davis, Sergeantsville, all of N.J.

[73] Assignee: Hoechst-Roussel Pharmaceuticals Inc., Somerville, N.J.

[21] Appl. No.: 372,508

[22] Filed: Jun. 28, 1989

[51] Int. Cl.$^5$ .............................................. A61K 31/435
[52] U.S. Cl. ..................... 514/349; 514/352; 514/353; 546/297; 546/307; 546/308
[58] Field of Search ....................... 546/297, 307, 308; 514/349, 352, 353

[56]  References Cited
U.S. PATENT DOCUMENTS

| | | | |
|---|---|---|---|
| 3,118,884 | 1/1964 | Clarke | 544/106 |
| 3,495,969 | 2/1970 | Driscoll | 71/94 |
| 3,576,616 | 4/1971 | Nowotny | 546/326 |
| 3,721,676 | 3/1973 | Witzel et al. | 546/307 |

FOREIGN PATENT DOCUMENTS

| | | | |
|---|---|---|---|
| 0069885 | 9/1987 | Australia | 546/111 |
| 0110405 | 6/1984 | European Pat. Off. | 546/307 |
| 2073736 | 10/1981 | United Kingdom | 546/307 |

OTHER PUBLICATIONS

Brewster et al., J. Heterocyclic Chem, vol. 15, 1975, pp. 1497-1499.
Butler et al, J. Med. Chem, vol. 24, pp. 346-350, 1981.
Ito et al, Chem. Pharm. Bull, vol. 26, No. 5, 1978, pp. 1375-1383.

Primary Examiner—John M. Ford
Assistant Examiner—Zinna Northington-Davis
Attorney, Agent, or Firm—Tatsuya Ikeda

[57]  ABSTRACT

There are described compounds of the formula

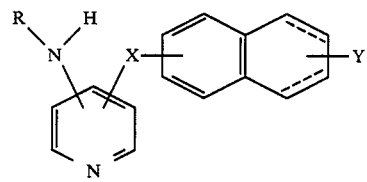

where
R is hydrogen, loweralkyl, arylloweralkyl or loweralkylcarbonyl;
X is O or NR$_1$, R$_1$ being hydrogen, loweralkyl or loweralkylcarbonyl; and
Y is hydrogen, loweralkyl, loweralkoxy, halogen or trifluoromethyl;

which compounds are useful as topical antiinflammatory agents for the treatment of skin disorders.

28 Claims, No Drawings

NAPHTHYLAMINO- AND NAPHTHYLOXY-PYRIDINAMINE COMPOUNDS USEFUL AS TOPICAL ANTIINFLAMMATORY AGENTS FOR THE TREATMENT OF SKIN DISORDERS

The present invention relates to compounds of Formula I,

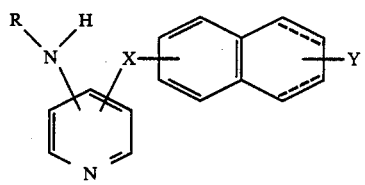

where
R is hydrogen, loweralkyl, arylloweralkyl or loweralkylcarbonyl;
X is O or $NR_1$, $R_1$ being hydrogen, loweralkyl or loweralkylcarbonyl; and
Y is hydrogen, loweralkyl, loweralkoxy, halogen or trifluoromethyl;
which compounds are useful as topical antiinflammatory agents for the treatment of various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis).

Also included within the scope of this invention are compounds of Formula II,

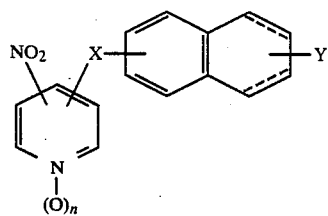

where X and Y are as defined earlier and n is 0 or 1, which compounds are useful for the same purpose as described above and also as direct precursors of compounds I.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean a phenyl group optionally mono-substituted with a loweralkyl, loweralkoxy, halogen or trifluoromethyl group.

Each of the dotted lines appearing in Formula I and other formulas used in this specification and appended claims signifies an optional double bond.

Throughout the specification and the appended claims, a given chemical formula or name shall encompass all stereo, optical, geometrical and tautomeric isomers where such isomers exist.

The compounds of this invention are prepared by utilizing one or more of the synthetic steps described below.

Throughout the description of the synthetic steps, the notations R, $R_1$, X, Y and n shall have the respective meanings given above unless otherwise stated or indicated, and other notations shall have the respective meanings defined in their first appearances unless otherwise stated or indicated.

Step A

A compound of Formula III where Hal is F or Cl, preferably F, is allowed to react with a compound of Formula IV to afford a compound of Formula V.

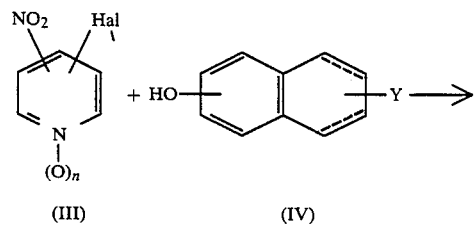

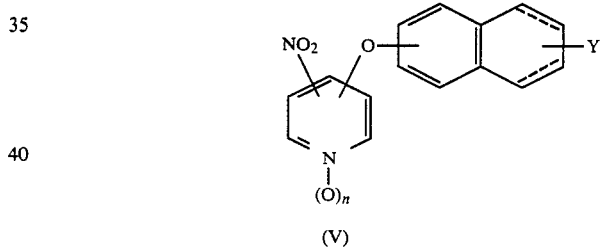

This reaction is typically conducted in the presence of an inorganic base such as sodium carbonate or potassium carbonate and a suitable solvent such as dimethylformamide at a temperature of about 0° to 150° C.

3-Fluoro-4-nitropyridine-N-oxide, which belongs to the group of compounds of Formula III, is disclosed in Talik and Talik, Roczniki Chemii, Volume 38,777 (1964). 4-Chloro-3-nitropyridine, which also belongs to the group of compounds of Formula III, is disclosed in Talik and Talik, Roczniki Chemii, Volume 43,923 (1969).

Step B

Compound III is allowed to react with a compound of Formula VI to afford a compound of Formula VII.

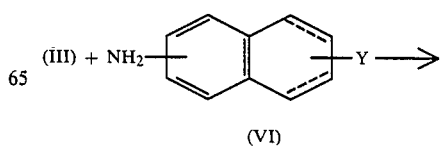

-continued

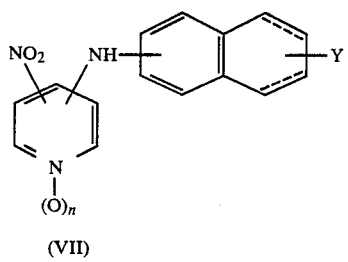

(VII)

This reaction is typically conducted in the presence of a suitable solvent such as ethanol, propanol, butanol, dimethylformamide, dimethylsulfoxide, or N-methylpyrrolidone at a temperature of about 0° to 150° C.

Step C

Compound VII is allowed to react with a compound of the formula, R$_2$-Hal, where R$_2$ is loweralkyl or loweralkylcarbonyl and Hal is bromine or chlorine in a routine manner known to the art to afford a compound of Formula VIII.

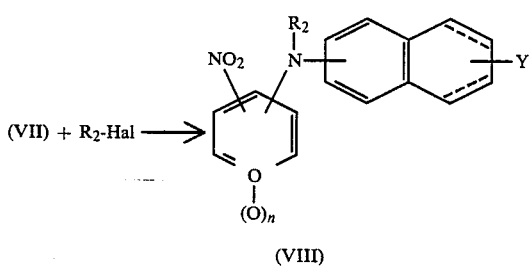

(VII) + R$_2$-Hal ⟶

(VIII)

Step D

A compound of Formula IX which is obtained from STEP A, B or C is catalytically hydrogenated to afford a compound of Formula X.

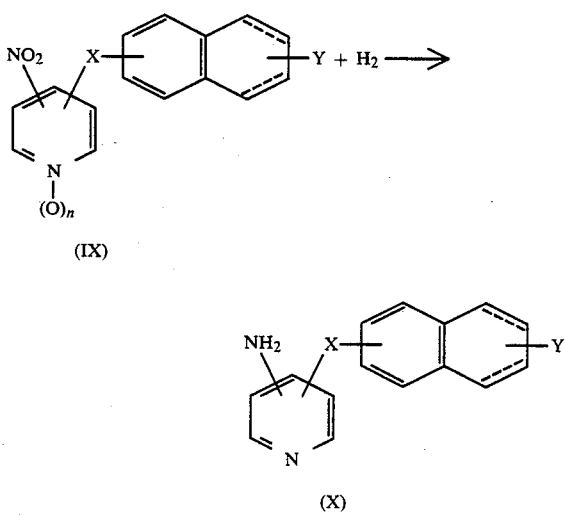

(IX)

(X)

This catalytic hydrogenation is typically conducted with a suitable catalyst such as Pd/C or PtO$_2$ and a suitable medium such as methanol, ethanol, propanol or butanol at a temperature of about 20° to 120° C.

Step E

Compound X is allowed to react with a compound of the formula, R$_3$-Hal, where R$_3$ is loweralkyl, aryllower-alkyl or loweralkylcarbonyl and Hal is bromine or chlorine, in a routine manner known to the art to afford a compound of Formula XI.

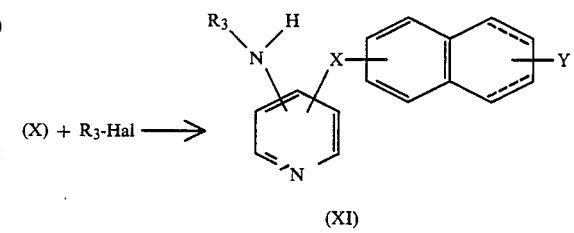

(X) + R$_3$-Hal ⟶

(XI)

Compounds of Formula I and Formula II according to this invention are useful as topical agents for the treatment of various skin disorders such as those mentioned earlier. The dermatological activities of the compounds of this invention were ascertained with reference to the following methods.

DERMATOLOGICAL TEST METHODS

Phospholipase A$_2$-induced Paw Edema (PIPE)

The ability of compounds to prevent naja naja (snake venom) phospholipase A$_2$-induced paw edema in male Wistar rats (100–125 g) was measured. PLA$_2$(3 units/paw) alone or with 0.1M of the test compound was injected in the subplantar region of the rat left hindpaw. Immediately subsequent to the injection and at two hours post administration the paw was immersed in a mercury bath, and paw displacement was measured on a recorder via a transducer. (Standard: hydrocortisone ED$_{50}$=0.46M). See Giessler, A. J. et al., *Agents and Actions*, Vol. 10, Trends in Inflammation Research (1981), p. 195.

In Vitro Phospholipase A$_2$ Assay (PLA$_2$)

The ability of a compound to modulate PLA$_2$-activity (cleavage of $^{14}$C-dipalmitoyl phosphotidylcholine at the 2-position to $^{14}$C-palmitic acid) was quantitated in this assay. The reaction mixture contained Tris buffer (25 mM), pH 8.0, calcium chloride (2.0 mM), bovine serum albumin (0.5 mg), dipalmitoyl phosphotidylcholine ($8 \times 10^{-5}$M), ($^{14}$C-palmitoyl)dipalmitoyl phosphotidylcholine ($6 \times 10^3$ cpm), porcine pancreatic PLA$_2$ (3.2 units) and the test compound. The reaction was run at 37° C. in a shaking incubator. The reaction was quenched and an internal standard was added in order to determine sample recovery. The samples were loaded onto C$_{18}$ columns, eluted with ethanol, and the radioactivity was then measured. (standard: quinacrine IC$_{50}$=$3.5 \times 10^{-4}$M). See Feyen, J. H. M., et al., Journal of Chromatography 259 (1983), pp. 338–340.

Arachidonic Acid-Induced Ear Edema (AAEE)

The purpose of this assay was to determine the ability of a topically-applied compound to prevent mouse ear edema induced by topical application of arachidonic acid. Female Swiss Webster mice topically received vehicle or test compound (1.0 mg/ear) on both ears (10 μl on outer and inner ears). After 30 minutes, the right ear of all groups received arachidonic acid (4 mg/ear) and the left ear received vehicle alone. After an additional 1 hour, the mice were sacrificed and an ear punch (4 mm) was taken from each ear. The difference in right and left ear punch weights for each animal was determined to assess activity. (Standard: indomethacin $ED_{50}=1.5$ mg/ear). See Young, J. M. et al., *Invest. Dermatol.*, 80, (1983), pp 48–52.

TPA-Induced Ear Edema (TPAEE)

The purpose of this assay was to determine the ability of a topically-applied compound to prevent ear edema induced by topical application of TPA (phorbol 12-myristate acetate). Female Swiss Webster mice topically received TPA (10 μg/ear) on the right ear and vehicle on the left ear. The test compound (10 μg/ear) was applied to both ears. After five hours, the animals were sacrificed and an ear punch (4 mm) was taken from each ear. The difference in right and left ear punch weights for each animal was determined to assess activity. (Standard: hydrocortisone $ED_{50}=47$ μg/ear). See Young, J. M. et al., *J. Invest. Dermatol.*, 80 (1983), pp. 48–52.

Cultured Human Keratinocyte DNA Synthesis (in vitro DNA)

The effect of a compound on the proliferation of cultured human epidermal keratinocytes was measured. After incubation with a test compound for 24 hours, the cultures were pulse-labelled for three hours with 5 μCi of $^3$H-thymidine. The cultures were extracted for DNA successively with trichloroacetic acid and ethanol, and thereafter dissolved with NaOH. The radioactive incorporation of $^3$H-thymidine into DNA was determined. (Standard: indomethacin $IC_{50}=3.8\times10^{-5}$M).

Epidermal DNA Synthesis (in vivo DNA)

The influence of compounds on the proliferation of skin was assessed by determining inhibition or stimulation of DNA synthesis. HRS/J hairless mice received topical application of a compound or vehicle alone on the dorsal aspect. After 24 hours, $^3$H-thymidine (25 μCi) was administered by intraperitoneal injection. After an additional hour, animals were sacrificed and the dorsal skin was removed. The epidermal layer was peeled from the dermis by heat separation. Unincorporated $^3$H-thymidine was removed by washing successively with trichloroacetic acid and ethanol. Samples were centrifuged at 2,000 rpm and supernatants discarded. The epidermal sheets were then extracted with warm trichloroacetic acid and the supernatants analyzed for $^3$H-thymidine incorporation by total DNA by a standard colorimetric assay. (Standard: indomethacin $ED_{50}=1.75$ mg/animal). See Lowe, N. J., et at., Arch. Dermatol., 117 (1981), pp. 394–8; and Burton, K., Biochem. J. 62 (1956), pp. 315–22.

Dermatological activities for some of the compounds of this invention are presented in

TABLE 1

| Compound | PIPE* (0.1 M) | PLA$_2$* (0.01 M) | AAEE (1 mg) | TPAEE (10 μg) |
|---|---|---|---|---|
| 3-(1-Naphthyloxy)-4-nitropyridine-N-oxide | | | | −27% |
| 3-(4-Chloro-1-naphthyloxy)-4-nitropyridine-N-oxide | | | | −41% |
| N-(1-Naphthyl)-4-nitro-3-pyridinamine-N-oxide | | | | −40% |
| 4-Nitro-3-(5,6,7,8-tetrahydro-1-naphthyloxy)-pyridine-N-oxide | | −38% | | |
| 3-(6-Bromo-2-naphthyloxy)-4-nitropyridine-N-oxide | | | | −43% |
| 4-(1-Naphthyloxy)-3-nitropyridine | | | | −72% |
| 4-(1-Naphthyloxy)-3-pyridinamine hydrochloride | | | | −40% |
| 3-(1-Naphthyloxy)-4-pyridinamine | −60% | −54% | −66% | |
| 3-(4-Methoxy-1-naphthyloxy)-4-pyridinamine | −40% | | | |
| 3-(4-Chloro-1-naphthyloxy)-4-pyridinamine oxalate | | −110% | | |
| 3-(5,6,7,8-Tetrahydro-1-naphthyloxy)-4-pyridinamine hydrochloride | | −110% | | |
| 3-(2-Naphthyloxy)-4-pyridinamine | | | −59% | |

*difference in edema vs. control

Examples of the compound of this invention include:
4-(1-Naphthyloxy)-3-pyridinamine;
3-(1-Naphthyloxy)-4-pyridinamine;
3-(4-Methoxy-1-naphthyloxy)-4-pyridinamine;
3-(4-Chloro-1-naphthyloxy)-4-pyridinamine;
3-(5,6,7,8-Tetrahydro-1-naphthyloxy)-4-pyridinamine;
3-(2-Naphthyloxy)-4-pyridinamine;
$N^3$-(2-Naphthyl)-3,4-pyridinediamine;
3-(5,6,7,8-Tetrahydro-2-naphthyloxy)-4-pyridinamine;
3-(1-Naphthyloxy)-4-nitropyridine-N-oxide;
3-(4-Methoxy-1-naphthyloxy)-4-nitropyridine-N-oxide;
3-(4-Chloro-1-naphthyloxy)-4-nitropyridine-N-oxide;
N-(1-Naphthyl)-4-nitro-3-pyridinamine-N-oxide;
4-Nitro-3-(5,6,7,8-tetrahydro-1-naphthyloxy)pyridine-N-oxide;
3-(2-Naphthyloxy)-4-nitropyridine-N-oxide;
3-(6-Bromo-2-naphthyloxy)-4-nitropyridine-N-oxide;
N-(2-Naphthyl)-4-nitro-3-pyridinamine-N-oxide;
4-Nitro-3-(5,6,7,8-tetrahydro-2-naphthyloxy)pyridine-N-oxide; and
4-(1-Naphthyloxy)-3-nitropyridine;

The following examples are presented in order to illustrate this invention:

EXAMPLE 1

3-(1-Naphthyloxy)-4-nitropyridine-N-oxide

To a solution of 1-naphthol (7.5 g) in 100 ml dimethylformamide (DMF) were added successively sodium carbonate (15 g) and 3-fluoro-4-nitropyridine-N-oxide[1]. After stirring one hour at ambient temperature, the reaction mixture was stirred with water and extracted with ethyl acetate. The organic extract was washed with water and saturated sodium chloride solution, dried (anhy. MgSO$_4$), filtered and concentrated to an oil. This oil was purified by flash chromatography (silica, 5% ethyl acetate in dichloromethane) to give 13 g oil. This oil was crystallized from ethanol to give 10.5 g solid, m.p. 105°. Three grams were recrystallized from ethanol to give crystals, 2.6 g, m.p. 106°–107°. [1]Talik and Talik, Roczniki Chemii 38,777 (1964)

Analysis: Calculated for $C_{15}H_{10}N_2O_4$: 63.83% C, 3.57% H, 9.92% N; Found: 63.87% C, 3.56% H, 9.85% N.

EXAMPLE 2

3-(4-Methoxy-1-naphthyloxy)-4-nitropyridine-N-oxide

To a solution of 4-methoxy-1-naphthol (8.87 g) in 50 ml of DMF was added sodium carbonate (7.8 g) portionwise, and after the addition was complete the mixture was stirred for 15 minutes. Then a solution of 3-fluoro-4-nitropyridine-N-oxide (8.0 g) in 50 ml DMF was added dropwise at room temperature. The reaction was then allowed to proceed for 4 hours at room temperature. The mixture was then poured into water and extracted with ethyl acetate. The organic layer was washed with NaCl (sat) and dried (anhy. $MgSO_4$).

After filtration, the solvent was evaporated to yield an oil which solidified on standing (31.0 g). This material was eluted with 10% ethyl acetate/DCM on silica gel columns via HPLC. The desired fractions were concentrated to yield a solid (14.2 g). Of this material 7.0 g was recrystallized from methanol to yield a solid, 2.6 g, m.p. 155°–157° C.

Analysis: Calculated for $C_{16}H_{12}N_2O_5$: 61.54% C, 3.87% H, 8.97% N; Found: 61.49% C, 3.86% H, 8.95% N.

EXAMPLE 3

3-(4-Chloro-1-naphthyloxy)-4-nitropyridine-N-oxide

To 75 ml dry DMF was added 4-chloro-1-naphthol (7.1 g), followed by $Na_2CO_3$ (8.0 g). After stirring at ambient temperature for fiteen minutes, a solution of 3-fluoro-4-nitropyridine-N-oxide (6.0 g) in 25 ml DMF was added in ten minutes.

After stirring at ambient temperature for 20 hours, the mixture was poured into 400 ml water, stirred for five minutes, and extracted with ethyl acetate (3×). The organic layer was washed with water (2×) and dried (sat. NaCl, anhydrous $MgSO_4$).

After filtration, the solvent was evaporated to afford 12 g of solid, m.p. 150°–155° C. This material was eluted on a silica gel column with 5% ethyl acetate/DCM via HPLC. The desired fractions were combined and concentrated to a solid, 11.0 g, m.p. 154°–155° C. A 3.0 g portion of this material was recrystallized from 300 ml methanol to afford needles, 2.5 g, m.p. 157°–158° C.

Analysis: Calculated for $C_{15}H_9ClN_2O_4$: 56.89% C, 2.86% H, 8.85% N; Found: 56.86% C, 2.87% H, 8.84% N.

EXAMPLE 4

N-(1-Naphthyl)-4-nitro-3-pyridinamine-N-oxide

To 1-naphthylamine (5.43 g) in 100 ml of absolute ethanol was added 3-fluoro-4-nitropyridine-N-oxide (6.0 g) in 25 ml of ethanol and this mixture was heated to 70° C. and stirred for six hours. The mixture was filtered to yield a solid (6.6 g) which was recrystallized from ethanol to yield a solid (2.6 g), m.p. 200°–201° C. (decomp.).

Analysis: Calculated for $C_{15}H_{11}N_3O_3$: 64.05% C, 3.94% H, 14.94% N; Found: 63.92% C, 3.95% H, 14.88% N.

EXAMPLE 5

4-Nitro-3-(5,6,7,8-tetrahydro-1-naphthyloxy)pyridine-N-oxide

To 5,6,7,8-tetrahydro-1-naphthol (6.0 g) in DMF (100 ml) was added $Na_2CO_3$ (10 g) portionwise at room temperature. Then a solution of 3-fluoro-4-nitropyridine-N-oxide (6.0 g) in 20 ml of DMF was added dropwise and the mixture was stirred at room temperature for four hours. The mixture was then poured into water and extracted with ethyl acetate. The organic layer was washed with water and dried (sat NaCl, anhy. $MgSO_4$).

After filtration, the solvent was evaporated to yield a solid (12.2 g), which was eluted with 2.5% ethyl acetate/DCM on a silica gel column via HPLC. The desired fractions were concentrated to yield a solid (9.8 g). Of this material, 4.8 g was recrystallized from absolute ethanol to yield a solid, 2.8 g, m.p. 109°–111° C.

Analysis: Calculated for $C_{15}H_{14}N_2O_4$: 62.93% C, 4.93% H, 9.79% N; Found: 62.93% C, 4.88% H, 9.74% N.

EXAMPLE 6

3-(2-Naphthyloxy)-4-nitropyridine-N-oxide

To a solution of 2-naphthol (7 g) in 50 ml dimethylformamide was added sodium carbonate (10 g), followed by 3-fluoro-4-nitropyridine-N-oxide. After stirring three hours at ambient temperature the reaction mixture was stirred with water and extracted with ethyl acetate. The organic extract was washed with water and saturated sodium chloride solution, dried (anhy. $MgSO_4$), filtered and concentrated to a solid. This solid was triturated with ether, collected and dried to give a solid, 11.6 g, m.p. 130°–133° C. A three gram portion was recrystallized from ethanol to give crystals, 2.8 g, m.p. 131°–133° C.

Analysis: Calculated for $C_{15}H_{10}N_2O_4$: 63.83% C, 3.57% H, 9.92% N; Found: 63.71% C, 3.48% H, 9.91% N.

EXAMPLE 7

3-(6-Bromo-2-naphthyloxy)-4-nitropyridine-N-oxide

To 6-bromo-2-naphthol (8.43 g) in 80 ml DMF at room temperature was added sodium carbonate (8.0 g) portionwise, and after the addition was complete, the mixture was stirred for 10 minutes, and then a solution of 3-fluoro-4-nitropyridine-N-oxide (6.0 g) in 40 ml DMF was added dropwise. The reaction mixture was then stirred for six hours at room temperature. The mixture was then poured into water and extracted with ethyl acetate. The organic layer was washed with sat. NaCl solution and dried over $Na_2SO_4$. The filtrate was concentrated to yield a solid (31 g). This material was triturated with methanol to yield a solid, 10.0 g, m.p. 175°–177° C.

Analysis: Calculated for $C_{15}H_9BrN_2O_4$: 49.89% C, 2.51% H, 7.76% N; Found: 49.60% C, 2.44% H, 7.55% N.

EXAMPLE 8

N-(2-Naphthyl)-4-nitro-3-pyridinamine-N-oxide

To 150 ml of ethanol were added 3-fluoro-4-nitropyridine-N-oxide (7.0 g) and 2-aminonaphthalene (6.6 g) and the mixture was heated to 70° C. and stirred for one hour. The mixture was cooled and filtered and the solid collected to yield a solid (11.5 g). A 2.5 g portion of this material was triturated with methanol to yield a solid, 2.5 g, m.p. 222°–224° C.

Analysis: Calculated for $C_{15}H_{11}N_3O_3$: 64.05% C, 3.94% H, 14.94% N; Found: 64.11% C, 3.86% H, 14.88% N.

EXAMPLE 9

4-Nitro-3-(5,6,7,8-tetrahydro-2-naphthyloxy)pyridine-N-oxide

To a solution of 5,6,7,8-tetrahydro-2-naphthol in 50 ml of DMF was added $Na_2CO_3$ (10 g) portionwise and this mixture was stirred for 15 minutes at room temperature. A solution of 3-fluoro-4-nitropyridine-N-oxide in 50 ml DMF was added dropwise and the reaction was allowed to proceed for four hours at room temperature. The mixture was poured into water and extracted with ethyl acetate. The organic layer was washed with water and dried (sat NaCl, anhy $MgSO_4$).

After filtration, the solvent was evaporated to yield an oil (12.2 g), which was eluted with 5% ethyl acetate/DCM on a silica gel column via HPLC. The desired fractions were concentrated to yield an oil, which solidified on standing (7.7 g). A 2.7 g portion of this material was recrystallized from ethanol to yield a solid, 2.0 g, m.p. 97°–99° C.

Analysis: Calculated for $C_{15}H_{14}N_2O_4$: 62.93% C, 4.93% H, 9.78% N; Found: 62.88% C, 4.82% H, 9.76% N.

EXAMPLE 10

4-(1-Naphthyloxy)-3-nitropyridine

To 50 ml of DMF was added 1-naphthol (11.25 g) and to this solution was added $K_2CO_3$ (20 g) portionwise. After stirring for 10 minutes at room temperature, 4-chloro-3-nitropyridine (11.2 g) in 60 ml of DMF was added dropwise. The reaction mixture was stirred for 4 hours at room temperature. The mixture was then poured into water and extracted with ethyl acetate. The organic layer was washed with water and dried (sat. NaCl, anhy. $MgSO_4$).

After filtration, the solvent was evaporated to yield an oil (25 g), which was eluted with DCM on silica gel columns via HPLC. The desired fractions were concentrated to yield a solid (14.7 g). Of this material, 5.0 g was recrystallized from ethanol to yield a solid, 2.7 g, m.p. 97°–100° C.

Analysis: Calculated for $C_{15}H_{10}N_2O_3$: 67.67% C, 3.79% H, 10.52% N; Found: 67.76% C, 3.77% H, 10.54% N.

EXAMPLE 11

4-(1-Naphthyloxy)-3-pyridinamine hydrochloride

To a slurry of 10% Pd/C (1.0 g) in 10 ml of ethanol was added 4-(1-naphthyloxy)-3-nitropyridine (10.4 g) in 240 ml of ethanol and this mixture was shaken on a Parr apparatus for 5 hours. The mixture was filtered and the filtrate concentrated to yield an oil (3.8 g) which was eluted with 50% ethyl acetate/DCM on a silica gel column via HPLC. The desired fractions were concentrated to yield an oil (2.65 g) which was dissolved in ethyl acetate and acidified with ethereal HCl. The resulting precipitate was collected to yield a solid, 2.5 g, m.p. 260° C. (decomp.).

Analysis: Calculated for $C_{15}H_{13}ClN_2O$: 66.06% C, 4.80% H, 10.27% N; Found: 65.82% C, 4.85% H, 10.14% N.

EXAMPLE 12

3-(1-Naphthyloxy)-4-pyridinamine

A suspension of 3-(1-naphthyloxy)-4-nitropyridine-N-oxide (7.5 g) in 250 ml ethanol containing 0.5 g $PtO_2$ was hydrogenated at 50 psi for five hours and filtered through Celite. The filtrate was concentrated to 6 g oil. This oil was purified by HPLC (silica, 50% ethyl acetate in dichloromethane) to give 4 g oil. Final purification was achieved by converting the oil to the hydrochloride salt in methanol/ether and immediately thereafter reconverting the salt to the free base with sodium carbonate to afford 3.5 g solid product. This solid was recrystallized from diethyl ether to give a solid, 2.3 g, m.p. 107°–109°.

Analysis: Calculated for $C_{15}H_{12}N_2O$: 76.25% C, 5.12% H, 11.86% N; Found: 76.34% C, 5.17% H, 11.80% N.

EXAMPLE 13

3-(4-Methoxy-1-naphthyloxy)-4-pyridinamine

To a slurry of $PtO_2$ (0.3 g) in 5 ml of ethanol was added 3-(4-methoxy-1-naphthyloxy)-4-nitropyridine-N-oxide (7.2 g) in 245 ml of ethanol. The material was hydrogenated under pressure (50 PSI) by shaking the slurry on a Parr apparatus for six hours. The mixture was filtered and the filtrate concentrated to yield an oil (5.2 g). This oil was eluted with 5% methanol/DCM on a silica gel column via HPLC. The desired fractions were concentrated to yield an oil which solidified on standing (4.36 g). This material was triturated with ether to yield a solid, 2.85 g, m.p. 126°–129° C.

Analysis: Calculated for $C_{16}H_{14}N_2O_2$: 72.17% C, 5.30% H, 10.52% N; Found: 71.95% C, 5.30% H, 10.48% N.

EXAMPLE 14

3-(4-Chloro-1-naphthyloxy)-4-pyridinamine oxalate

To 250 ml ethanol in a 500 ml Parr hydrogenation bottle were added 3-(4-chloro-1-naphthyloxy)-4-nitropyridine-N-oxide (4.0 g) and 0.4 g $PtO_2$.

After shaking under hydrogen for twelve hours at 50 psi, the mixture was filtered, and the filtrate was concentrated to 3.5 g of oil, which was eluted on a silica gel column with 2% methanol/DCM via HPLC. The desired fractions were combined and concentrated to a thick oil, which solidified on standing to afford, 2.4 g of solid, m.p. 130°–132° C.

This material was dissolved in ether, the pH was adjusted to 1 with ethereal oxalic acid, and the resultant precipitate collected and dried to give 1.8 g, m.p. 125° C. This material was recrystallized from methanol/ether (1:3) to yield 1.2 g of precipitate, d @ 187° C.

Analysis: Calculated for $C_{15}H_{11}ClN_2O \cdot C_2H_2O_4$: 56.60% C, 3.63% H, 7.77% N; Found: 56.94% C, 3.86% H, 7.75% N.

EXAMPLE 15

3-(5,6,7,8-Tetrahydro-1-naphthyloxy)-4-pyridinamine hydrochloride

To a slurry of $PtO_2$ (0.25 g) in 10 ml of ethanol was added 4-nitro-3-(5,6,7,8-tetrahydro-1-naphthyloxy)-pyridine-N-oxide (5.0 g) in 240 ml of ethanol. This was hydrogenated at 60 psi for four hours on a Parr apparatus. The mixture was filtered and the filtrate concentrated to yield an oil (4.26 g). This material was eluted with 7.5% methanol/DCM on a silica gel column via HPLC. The desired fractions were concentrated to yield an oil (3.9 g). This material was converted to the HCl salt with ethereal HCl in methanol. The resulting precipitate was collected to yield a solid (3.3 g) which was recrystallized from methanol/ether (1:5). The resulting crystals were collected to yield 2.65 g, m.p. 241°–243° C.

Analysis: Calculated for $C_{15}H_{17}ClN_2O$: 65.10% C, 6.19% H, 10.12% N; Found: 65.53% C, 6.18% H, 10.18% N.

EXAMPLE 16

3-(2-Naphthyloxy)-4-pyridinamine

A suspension of 3-(2-naphthyloxy)-4-nitropyridine-N-oxide (8.5 g) in 250 ml ethanol containing 0.5 g platinum oxide was hydrogenated for 20 hours at 60 psi and thereafter filtered through Celite. The filtrate liquid was concentrated to 8.3 g oil. This oil was purified by flash chromatography (silica, ethyl acetate) to give a solid (7 g). This solid was recrystallized from anhydrous ether to give crystals, 4.6 g, mp 117°–118° C.

Analysis: Calculated for $C_{15}H_{12}N_2O$: 76.25% C, 5.12% H, 11.86% N; Found: 76.23% C, 5.08% H, 11.91% N.

EXAMPLE 17

$N^3$-(2-Naphthyl)-3,4-pyridinediamine maleate

To $PtO_2$ (0.3 g) suspended in 10 ml of ethanol was added N-(2-naphthyl)-4-nitro-3-pyridinamine-N-oxide (5.0 g) in 240 ml of ethanol and this mixture was hydrogenated on a Parr apparatus for 48 hours. The mixture was filtered and the filtrate concentrated to yield a solid (3.62 g), which was eluted with 15% methanol/DCM on a silica gel column via HPLC. The desired fractions were concentrated to yield an oil (2.5 g), which was converted to the maleate salt. This salt was then recrystallized from methanol/ether (1:5) to yield a solid, 1.6 g, m.p. 170°–171° C.

Analysis: Calculated for $C_{15}H_{13}N_3 \cdot C_4H_4O_4$: 64.95% C, 4.88% H, 11.96% N; Found: 64.85% C, 4.88% H, 11.90% N.

EXAMPLE 18

3-(5,6,7,8-Tetrahydro-2-naphthyloxy)-4-pyridinamine hydrochloride

To a suspension of $PtO_2$ in 5 ml of ethanol was added 4-nitro-3-(5,6,7,8-tetrahydro-2-naphthyloxy)pyridine-N-oxide in 245 ml of ethanol. This was hydrogenated on a Parr apparatus for four hours. The mixture was filtered and the filtrate concentrated to yield an oil (3.81 g). This material was eluted with 7.5% methanol/DCM on a silica gel column via HPLC. The desired fractions were concentrated to yield an oil (3.34 g), which was converted to the HCl salt in methanol with ethereal HCl. The resulting precipitate (3.1 g) was recrystallized from methanol/ether (1:5) to yield a solid, 2.2 g, m.p. 170°–172° C.

Analysis: Calculated for $C_{15}H_{17}ClN_2O$: 65.10% C, 6.19% H, 10.12% N; Found: 64.99% C, 6.19% H, 10.06% N.

We claim:

1. A compound of the formula

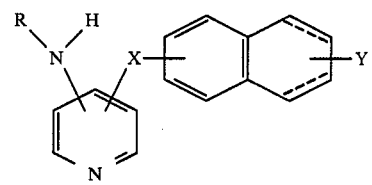

where
R is hydrogen, loweralkyl, arylloweralky or loweralkylcarbonyl;
X is O or $NR_1$, $R_1$ being hydrogen, loweralkyl or loweralkylcarbonyl; and
Y is hydrogen, loweralkyl, loweralkoxy, halogen or trifluoromethyl;
the term aryl signifying a phenyl group optionally mono-substituted with a loweralkyl, loweralkoxy, halogen or trifluoromethyl group, or a pharmaceutically acceptable acid addition salt thereof.

2. The compound as defined in claim 1, where R is hydrogen.

3. The compound as defined in claim 1, where X is O or NH.

4. The compound as defined in claim 1, where R is hydrogen and X is O or NH.

5. The compound as defined in claim 1, which is 4-(1-naphthyloxy)-3-pyridinamine.

6. The compound as defined in claim 1, which is 3-(1-naphthyloxy)-4-pyridinamine.

7. The compound as defined in claim 1, which is 3-(4-methoxy-1-naphthyloxy)-4-pyridinamine.

8. The compound as defined in claim 1, which is 3-(4-chloro-1-naphthyloxy)-4-pyridinamine.

9. The compound as defined in claim 1, which is 3-(5,6,7,8-tetrahydro-1-naphthyloxy)-4-pyridinamine.

10. The compound as defined in claim 1, which is 3-(2-naphthyloxy)-4-pyridinamine.

11. The compound as defined in claim 1, which is $N^3$-(2-naphthyl)-3,4-pyridinediamine.

12. The compound as defined in claim 1, which is 3-(5,6,7,8-tetrahydro-2-naphthyloxy)-4-pyridinamine.

13. A compound having the formula,

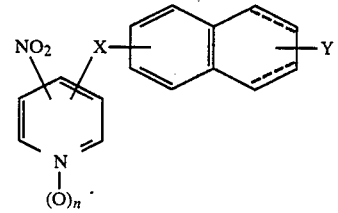

where
n is 0 or 1;
X is O or $NR_1$, $R_1$ being hydrogen, loweralkyl or loweralkylcarbonyl; and
Y is hydrogen, loweralkyl, loweralkoxy, halogen or trifluoromethyl;
or a pharmaceutically acceptable acid addition salt thereof.

14. The compound as defined in claim 13, where X is O or NH.

15. The compound as defined in claim 13, which is 3-(1-naphthyloxy)-4-nitropyridine-N-oxide.

16. The compound as defined in claim 13, which is 3-(4-methoxy-1-naphthyloxy)-4-nitropyridine-N-oxide.

17. The compound as defined in claim 13, which is 3-(4-chloro-1-naphthyloxy)-4-nitropyridine-N-oxide.

18. The compound as defined in claim 13, which is N-(1-naphthyl)-4-nitro-3-pyridinamine-N-oxide.

19. The compound as defined in claim 13, which is 4-nitro-3-(5,6,7,8-tetrahydro-1-naphthyloxy)pyridine-N-oxide.

20. The compound as defined in claim 13, which is 3-(2-naphthoxy)-4-nitropyridine-N-oxide.

21. The compound as defined in claim 13, which is 3-(6-bromo-2-naphthyloxy)-4-nitropyridine-N-oxide.

22. The compound as defined in claim 13, which is N-(2-naphthyl)-4-nitro-3-pyridinamine-N-oxide.

23. The compound as defined in claim 13, which is 4-nitro-3-(5,6,7,8-tetrahydro-2-naphthyloxy)pyridine-N-oxide.

24. The compound as defined in claim 13, which is 4-(1-naphthyloxy)-3-nitropyridine.

25. A dermatological composition comprising a compound as defined in claim 1 in an amount effective for treating a dermatosis and a suitable carrier therefor.

26. A dermatological composition comprising a compound as defined in claim 13 in an amount effective for treating a dermatosis and a suitable carrier therefor.

27. A method of treating a patient in need of relief from dermatosis which comprises administering to such a patient an effective amount of a compound as defined in claim 1.

28. A method of treating a patient in need of relief from dermatosis which comprises administering to such a patient an effective amount of a compound as defined in claim 13.

* * * * *

REEXAMINATION CERTIFICATE (2135th)
United States Patent [19]
Effland et al.

[11] B1 4,931,457
[45] Certificate Issued Nov. 16, 1993

[54] NAPHTHYLAMINO-AND NAPHTHYLOXY-PYRIDINEAMIN COMOUNDS USEFUL AS TOPICAL ANTIINFLAMMATORY AGENTS FOR THE TREATMENT OF SKIN DISORDERS

[75] Inventors: Richard C. Effland; Joseph T. Klein, both of Bridgewater; Gordon E. Olsen, Somerset; Larry Davis, Sergeantsville, all of N.J.

[73] Assignee: Hoechst-Roussel Pharmaceuticals Incorporated, Bridgewater, N.J.

Reexamination Request:
No. 90/002,767, Jun. 30, 1992

Reexamination Certificate for:
Patent No.: 4,931,457
Issued: Jun. 5, 1990
Appl. No.: 372,508
Filed: Jun. 28, 1989

[51] Int. Cl.$^5$ ............... A61K 31/435; C07D 213/72; C07D 213/75
[52] U.S. Cl. .................. 514/49; 514/352; 514/353; 546/297; 546/307; 546/308
[58] Field of Search .............. 546/297, 307, 308; 514/349, 352, 353

[56] References Cited
U.S. PATENT DOCUMENTS
4,521,426  6/1985  Cain .................................. 514/346

OTHER PUBLICATIONS
Archiv Der Pharmazie, vol. 321, 1988, pp. 463–466.
Chemica Scripta, vol. 25, No. 4, 1985, pp. 350–355.
Journal of Medicinal Chemistry, vol. 21, No. 9, 1978, pp. 965–978.
ACS Symp Ser., 233 (NonLinear Optical Properties Org. Polym. Mater.), 1983, pp. 57–80.
Polish Journal of Pharmacology and Pharmacy, vol. 42, No. 2, 1990, pp. 165–175.

*Primary Examiner*—Alan L. Rotman

[57] ABSTRACT

There are described compounds of the formula

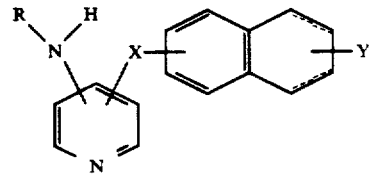

where

R is hydrogen, loweralkyl, arylloweralkyl or loweralkylcarbonyl;

X is O or $NR_1$, $R_1$ being hydrogen, loweralkyl or loweralkylcarbonyl; and

Y is hydrogen, loweralkyl, loweralkoxy, halogen or trifluoromethyl;

which compounds are useful as topical antiinflammatory agents for the treatment of skin disorders.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 13, 25–28 are determined to be patentable as amended.

Claims 2–12 and 14–24, dependent on an amended claim, are determined to be patentable.

1. A compound of the formula

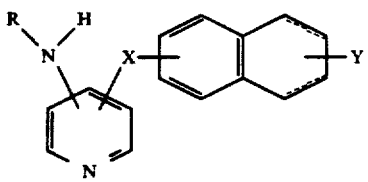

where
- R is hydrogen, loweralkyl, arylloweralkyl or loweralkylcarbonyl;
- X is O or NR$_1$, R$_1$ being hydrogen, loweralkyl or loweralkylcarbonyl; and
- Y is hydrogen, loweralkyl, loweralkoxy, halogen or trifluoromethyl;
- the term aryl signifying a phenyl group optionally mono-substituted with a loweralkyl, loweralkoxy, halogen or trifluoromethyl group, or a pharmaceutically acceptable acid addition salt thereof; *where the*

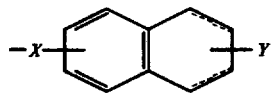

*group and the NHR group are ortho to each other and attached at the 3- and 4-positions of the pyridine.*

13. A compound having the formula

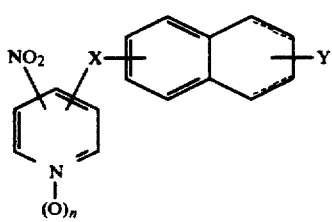

where
n is 0 or 1;

X is O or NR$_1$, R$_1$ being hydrogen, loweralkyl or loweralkylcarbonyl; and
Y is hydrogen, loweralkyl, loweralkoxy, halogen or trifluoromethyl;
or a pharmaceutically acceptable acid addition salt thereof; *where the*

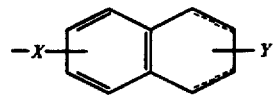

*group and the NO$_2$ group are ortho to each other and attached at the 3- and 4-position of the pyridine and with the proviso that when the NO$_2$ group is at the 3-position of pyridine and n is 0, the*

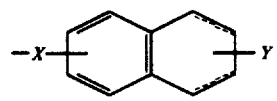

*group is not 4-(1-naphthylamino).*

25. A dermatological composition comprising a compound [as defined in claim 1] *of the formula*

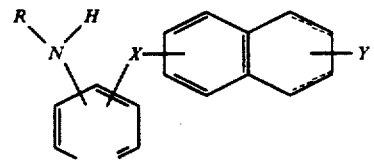

*where*
- *R is hydrogen, loweralkyl, arylloweralkyl or loweralkylcarbonyl;*
- *X is O or NR$_1$, R$_1$ being hydrogen, loweralkyl or loweralkylcarbonyl; and*
- *Y is hydrogen, loweralkyl, loweralkoxy, halogen or trifluoromethyl;*
- *the term aryl signifying a phenyl group optionally mono-substituted with a loweralkyl, loweralkoxy, halogen or trifluoromethyl group, or a pharmaceutically acceptable acid addition salt thereof;* in an amount effective for treating a dermatosis and a suitable carrier therefor.

26. A dermatological composition comprising a compound [as defined in claim 13] *of the formula*

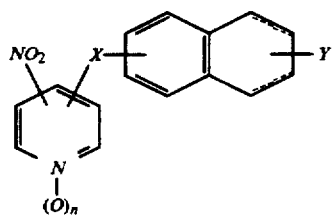

*where*
*n is 0 or 1;*
*X is O or NR$_1$, R$_1$ being hydrogen, loweralkyl or loweralkylcarbonyl; and*
*Y is hydrogen, loweralkyl, loweralkoxy, halogen or trifluoromethyl;* or a pharmaceutically acceptable acid addition salt thereof in an amount effective for treating a dermatosis and a suitable carrier thereof.

27. A method of treating a patient in a need of relief from dermatosis which comprises administering to such a patient an effective amount of a compound [as defined in claim 1] of the formula

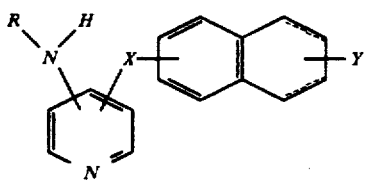

where
R is hydrogen, loweralkyl, arylloweralkyl or loweralkylcarbonyl;
X is O or NR₁, R₁ being hydrogen, loweralkyl or loweralkylcarbonyl; and
Y is hydrogen, loweralkyl, loweralkoxy, halogen or trifluoromethyl;
or a pharmaceutically acceptable acid addition salt thereof.

28. A method of treating a patient in need of relief from dermatosis which comprises administering to such a patient an effective amount of a compound [as defined in claim 13] of the formula

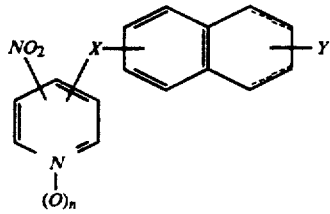

where
n is 0 or 1;
X is O or NR₁, R₁ being hydrogen, loweralkyl or loweralkylcarbonyl; and
Y is hydrogen, loweralkyl, loweralkoxy, halogen or trifluoromethyl;
or a pharmaceutically acceptable acid additional salt thereof.

* * * * *